United States Patent [19]
Henkelmann et al.

[11] Patent Number: 5,646,293
[45] Date of Patent: Jul. 8, 1997

[54] PREPARATION OF N-ALKENYLAZOLES

[75] Inventors: Jochem Henkelmann, Mannheim; Marc Heider, Neustadt; Thomas Rühl, Frankenthal, all of Germany

[73] Assignee: BASF Aktiengesellschaft, Ludwigshafen, Germany

[21] Appl. No.: 675,588

[22] Filed: Jul. 3, 1996

[30] Foreign Application Priority Data

Jul. 6, 1995 [DE] Germany .................. 195 24 618.7

[51] Int. Cl.$^6$ .................. C07D 249/08; C07D 235/08; C07D 235/18; C07D 233/58

[52] U.S. Cl. .................. 548/262.2; 548/262.4; 548/267.8; 548/268.4; 548/304.4; 548/310.1; 548/310.4; 548/310.7; 548/335.1; 548/341.1; 548/342.5; 548/343.1; 548/343.5; 548/345.1

[58] Field of Search .................. 548/262.2, 262.4, 548/267.8, 268.4, 304.4, 310.1, 310.4, 310.7, 335.1, 341.1, 342.5, 343.1, 343.5, 345.1

[56] References Cited

PUBLICATIONS

Stotskii et al, "Synthesis and study of 1-vinyl, etc" CA 106: 156361 m (1987).

*Primary Examiner*—Patricia L. Morris
*Attorney, Agent, or Firm*—John H. Shurtleff

[57] ABSTRACT

A process for preparing N-alkenylazoles of the general formula I

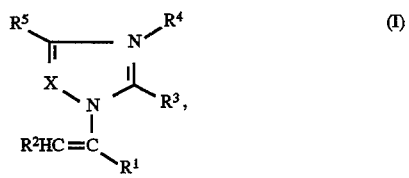

where

X is CH—$R^6$ or nitrogen, $R^1$ and $R^2$ are hydrogen or $C_1$- to $C_8$-alkyl, $R^3, R^4, R^5$ and $R^6$ are hydrogen, $C_1$- to $C_{40}$-alkyl, $C_2$- to $C_{40}$-alkenyl, $C_3$- to $C_{20}$-cycloalkyl, $C_4$- to $C_{20}$-alkylcycloalkyl, $C_4$- to $C_{20}$-cycloalkylalkyl, aryl, $C_7$- to $C_{20}$-alkylaryl or $C_7$- to $C_{20}$-aralkyl, or aryl, $C_7$- to $C_{20}$-alkylaryl or $C_7$- to $C_{20}$-aralkyl which are mono- to pentasubstituted by $C_1$- to $C_8$-alkyl, $C_1$- to $C_8$-alkoxy or halogen, or $R^3$ and $R^4$ or $R^4$ and $R^5$ or $R^5$ and $R^6$ together are a $C_2$- to $C_{10}$-alkylene chain which is unsubstituted or mono- to hexasubstituted by $C_1$- to $C_8$-alkyl by reaction of azoles of the general formula II

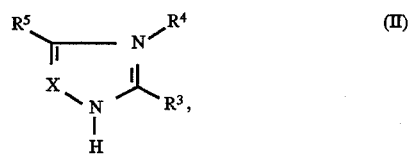

where X, $R^3$, $R^4$ and $R^5$ have the abovementioned meanings, with an alkenyl carboxylate of the general formula III

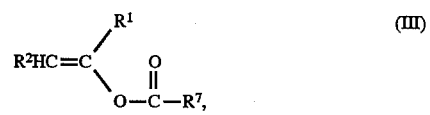

where $R^1$ and $R^2$ have the abovementioned meanings and $R^7$ is hydrogen, $C_1$- to $C_{40}$-alkyl, $C_3$- to $C_{20}$-cycloalkyl, $C_4$- to $C_{20}$-alkylcycloalkyl, aryl, $C_7$- to $C_{20}$-alkylaryl, $C_7$- to $C_{20}$-aralkyl, or aryl or $C_7$- to $C_{20}$-aralkyl which is mono- to trisubstituted by $C_1$- to $C_8$-alkyl, at from 0° to 180° C. and from 0.01 to 10 bar, which comprises carrying out the reaction in the presence of a base and of a quaternary salt, is described.

16 Claims, No Drawings

PREPARATION OF N-ALKENYLAZOLES

The present invention relates to a novel process for preparing N-alkenylazoles by reaction of azoles with an alkenyl carboxylate at elevated temperatures in the presence of a base and subsequently with addition of a quaternary salt.

Liebigs Annalen der Chemie, Volume 601 (1956), page 133 ff. discloses the preparation of N-vinylimidazoles by reaction of imidazoles with acetylene under pressure in the presence of bases.

Working with acetylene requires a large industrial outlay with regard to acetylene availability and safe working with acetylene. Attention is particularly to be given to the safe conduct of the reaction, as the catalyst potassium hydroxide used for the reaction of imidazoles with acetylene can induce decomposition of acetylene in the reaction system. Recent investigations by Schildberg et al. have shown this (Chem. Ing. Tech. 66 (1994) 1389 to 1392).

It is therefore an object of the present invention to remedy the abovementioned disadvantages.

We have found that this object is achieved by a novel and improved process for preparing N-alkenylazoles of the general formula I

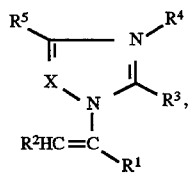

where

X is CH—$R^6$ or nitrogen, $R^1$ and $R^2$ are hydrogen or $C_1$- to $C_8$-alkyl, $R^3$, $R^4$, $R^5$ and $R^6$ are hydrogen, $C_1$- to $C_{40}$-alkyl, $C_2$- to $C_{40}$-alkenyl, $C_3$- to $C_{20}$-cycloalkyl, $C_4$- to $C_{20}$-alkylcycloalkyl, $C_4$- to $C_{20}$-cycloalkylalkyl, aryl, $C_7$- to $C_{20}$-alkylaryl or $C_7$- to $C_{20}$-aralkyl, or aryl, $C_7$- to $C_{20}$-alkylaryl or $C_7$- to $C_{20}$-aralkyl which are mono- to pentasubstituted by $C_1$- to $C_8$-alkyl, $C_1$- to $C_8$-alkoxy or halogen, or $R^3$ and $R^4$ or $R^4$ and $R^5$ or $R^5$ and $R^6$ together are a $C_2$- to $C_{10}$-alkylene chain which is unsubstituted or mono- to hexasubstituted by $C_1$- to $C_8$-alkyl by reaction of azoles of the general formula II

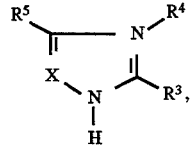

where X, $R^3$, $R^4$ and $R^5$ have the abovementioned meanings, with an alkenyl carboxylate of the general formula III

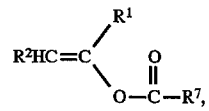

where $R^1$ and $R^2$ have the abovementioned meanings and $R^7$ is hydrogen, $C_1$- to $C_{40}$-alkyl, $C_3$- to $C_{20}$-cycloalkyl, $C_4$- to $C_{20}$-alkylcycloalkyl, aryl, $C_7$- to $C_{20}$-alkylaryl, $C_7$- to $C_{20}$-aralkyl, or aryl or $C_7$- to $C_{20}$-aralkyl which is mono- to trisubstituted by $C_1$- to $C_8$-alkyl, at from 0° to 180° C. and from 0.01 to 10 bar, which comprises carrying out the reaction in the presence of a base and of a quaternary salt.

The process according to the invention can be carried out as follows:

The azoles II and the alkenyl carboxylates III can be reacted continuously or batchwise in the presence or, preferably, in the absence of the addition of an inert solvent at from 0° to 180° C., preferably 40° to 150° C., particularly preferably 50° to 120° C. and from 0.01 to 10 bar, preferably 0.1 to 2 bar, particularly preferably atmospheric pressure (normal pressure) in the presence of a base and of a quaternary salt, it being possible to mix together the starting materials in any desired sequence. The starting compounds II and III, the base and the quaternary salt can thus be added, for example, in a stirring vessel and reacted therein. It is also possible to react the starting compounds II and III, the base and the quaternary salt in a tubular reactor, for example in a trickle or liquid-phase procedure. It has proven advantageous to perform the reaction in a jet nozzle reactor.

Suitable bases are inorganic or organic bases, preferably Brönsted bases, eg. carbonates and hydrogen carbonates of the alkali metals and alkaline earth metals such as sodium carbonate, potassium carbonate and sodium hydrogen carbonate, quaternary ammonium carbonates such as tetramethylammonium carbonate, amides such as alkali metal amides, for example sodium amide and potassium amide, hydroxides such as alkali metal hydroxides, for example lithium hydroxide, sodium hydroxide and potassium hydroxide, alkali metal carboxylates such as sodium acetate, alkoxides such as alkali metal alkoxides, for example sodium methoxide, sodium ethoxide, potassium ethoxide and potassium tert-butoxide. Potassium hydroxide can also be used together with crown ethers such as 18-crown-6.

Suitable bases are furthermore ammonia, and primary, secondary and tertiary amines, preferably tertiary amines. The amines can carry aliphatic or aromatic radicals, for example trialkylamines such as trioctylamine, ethyldiisopropylamine, diethylisopropylamine, dimethylcyclohexylamine, triethylamine, additionally cyclic amines such as 2,2,6,6-tetramethylpiperidine, 1,4-diazabicyclo[2.2.2]octane, 1,8-diazabicyclo[5.4.0]undec-7-ene, amines carrying aliphatic and aromatic radicals, such as 1,8-bis(dimethylamino)naphthalene and 4-dimethylaminopyridine and heterocyclic amines Such as N-alkylimidazoles and N-arylimidazoles. Amides such as dialkylcarboxamides, eg. dibutylformamide, are furthermore suitable. The process according to the invention can also be carried out in the presence of basic ion exchangers which generally consist of sulfonated styrene/divinylbenzene copolymers such as Amberlite®, Lewatit® and Puralit®, and in the presence of basic zeolites such as hydrotalcite.

Suitable quaternary salts are, for example, quaternary ammonium salts and quaternary phosphonium salts such as tetramethylphosphonium chloride, tetramethylammonium chloride, tetraethylphosphonium chloride, tetraethylammonium chloride, tetramethylphosphonium bromide, tetramethylammonium bromide, tetraethylphosphonium bromide, tetraethylammonium bromide, N,N-dimethylpiperidinium chloride and trimethylbenzylammonium chloride, preferably tetraethylammonium bromide, particularly preferably N,N'-dimethylpiperidinium chloride.

The molar ratio of alkenyl carboxylate III to the azole II is generally from 0.1:1 to 10:1, preferably 0.9:1 to 5:1, particularly preferably 1:2 to 1.2:1.

The molar ratio of base to the azole II is generally from 0.1:1 to 10:1, preferably 0.2:1 to 4:1, particularly preferably 0.2:1 to 2:1.

The molar ratio of quaternary salt to the azole II is generally from 0.0001:1 to 5:1, preferably 0.1:1 to 0.8:1, particularly preferably 0.001:1 to 0.4:1.

Suitable inert solvents are, for example, aprotic solvents, eg. ethers such as tetrahydrofuran, aromatic hydrocarbons such as toluene and xylene, ketones such as acetone, furthermore acetonitrile, hexamethylphosphoramide, sulfolane, dimethyl sulfoxide, ureas such as N,N'-dimethylethyleneurea, N,N'-dimethylpropyleneurea and tetrabutylurea. The amount is generally from 5 to 300% by weight, preferably 10 to 100% by weight, particularly preferably 10 to 30% by weight, based on the total mixture.

Generally, the reaction is complete after from 5 minutes to 8 hours.

The reaction mixture thus obtained can be worked up in a manner known per so. Generally, the N-alkenylazole I is removed by distillation. The distillation bottom can be treated with alkalis such as sodium hydroxide solution to release the organic bases from the salts formed in the reaction. The bases employed can then be isolated by extraction or distillation. If, in the reaction according to the invention, readily volatile salt-like compounds such as formates of tertiary ammonium compounds are formed, these can also be worked up by distillation and converted into the corresponding amines. The bases separated off in each case can be fed back into the reaction.

The substituents $R^1$, $R^2$, $R^3$, $R^4$, $R^5$, $R^6$, $R^7$ and the intermediate member X in the compounds I, II and III have the following meanings:

X is

CH—$R^6$, nitrogen, $R^1$, $R^2$, $R^3$, $R^4$, $R^5$, $R^6$ and $R^7$ are hydrogen, $R^1$ and $R^2$ are $C_1$- to $C_8$-alkyl, preferably $C_1$- to $C_4$-alkyl such as methyl, ethyl, n-propyl, isopropyl, n-butyl, isobutyl, sec-butyl and tert-butyl, particularly preferably methyl and ethyl, $R^3$, $R^4$, $R^5$, $R^6$ and $R^7$ are $C_3$- to $C_{20}$-cycloalkyl, preferably $C_3$- to $C_{12}$-cycloalkyl, particularly preferably $C_5$- to $C_8$-cycloalkyl such as cyclopentyl, cyclohexyl, cycloheptyl and cyclooctyl, $C_4$- to $C_{20}$-alkylcycloalkyl, preferably $C_4$- to $C_{12}$-alkylcycloalkyl, aryl such as phenyl, 1-naphthyl and 2-naphthyl, preferably phenyl, $C_7$- to $C_{20}$-alkylaryl, preferably $C_7$- to $C_{16}$-alkylaryl, preferably $C_7$- to $C_{12}$-alkylphenyl such as 2-methylphenyl, 3-methylphenyl, 4-methylphenyl, 2-ethylphenyl, 3-ethylphenyl and 4-ethylphenyl, $C_7$- to $C_{20}$-aralkyl, preferably $C_7$- to $C_{16}$-aralkyl, preferably $C_7$- to $C_{12}$-phenalkyl such as phenylmethyl, 1-phenylethyl and 2-phenylethyl, $R^3$, $R^4$, $R^5$ and $R^6$ are $C_1$- to $C_{40}$-alkyl, preferably $C_1$- to $C_{12}$-alkyl, particularly preferably $C_1$- to $C_8$-alkyl such as methyl, ethyl, n-propyl, isopropyl, n-butyl, isobutyl, sec-butyl, tert-butyl, n-pentyl, isopentyl, n-hexyl, isohexyl, n-heptyl, isoheptyl, n-octyl and isooctyl, $C_2$- to $C_{40}$-alkenyl, preferably $C_2$- to $C_{12}$-alkenyl, particularly preferably $C_2$- to $C_8$-alkenyl such as vinyl and propenyl, $C_4$- to $C_{20}$-cycloalkylalkyl, preferably $C_4$- to $C_{12}$-cycloalkylalkyl, particularly preferably $C_5$- to $C_{10}$-cycloalkylalkyl, aryl which is mono- to pentasubstituted by $C_1$- to $C_8$-alkyl, $C_1$- to $C_8$-alkoxy or halogen, preferably phenyl which is mono- to trisubstituted by $C_1$- to $C_8$-alkyl, $C_1$- to $C_8$-alkoxy or halogen, such as tolyl and anisyl, $C_7$- to $C_{20}$-alkylaryl which is mono- to pentasubstituted by $C_1$- $C_8$-alkyl, $C_1$- to $C_8$-alkoxy or halogen, preferably $C_7$- to $C_{16}$-alkylphenyl which is mono- to trisubstituted by $C_1$- to $C_8$-alkyl, $C_1$- to $C_8$-alkoxy or halogen, $C_7$- to $C_{20}$-aralkyl which is mono- to pentasubstituted by $C_1$- to $C_8$-alkyl, $C_1$- to $C_8$-alkoxy or halogen, preferably $C_7$- to $C_{16}$-phenalkyl which is mono- to trisubstituted by $C_1$- to $C_8$-alkyl, $C_1$- to $C_8$-alkoxy or halogen, together a $C_2$- to $C_{10}$-alkylene chain, preferably a $C_2$- to $C_8$-alkylene chain, particularly preferably —$(CH_2)_2$-, —$(CH_2)_3$—, —$(CH_2)_4$— and —$(CH_2)_5$—, in particular —$(CH_2)_2$— and —$(CH_2)3$-, together a $C_2$- to $C_{10}$-alkylene chain which is unsubstituted or mono- to hexasubstituted by $C_1$- to $C_8$-alkyl, preferably together a $C_2$- to $C_8$-alkylene chain which is unsubstituted or mono- to trisubstituted by $C_1$- to $C_4$-alkyl, $R^7$ is $C_1$- to $C_{40}$-alkyl, preferably $C_1$- to $C_{20}$-alkyl, particularly preferably methyl, ethyl, n-propyl, isopropyl, n-butyl, tert-butyl, n-pentyl, n-hexyl, n-heptyl, n-octyl, n-decyl, n-dodecyl and n-octadecyl, aryl which is mono- to trisubstituted by $C_1$- to $C_8$-alkyl, preferably phenyl which is mono- to trisubstituted by $C_1$- to $C_4$-alkyl, such as 2-methylphenyl, $C_7$- to $C_{20}$-aralkyl which is mono- to trisubstituted by $C_1$- to $C_8$-alkyl, preferably $C_7$- to $C_{16}$-phenalkyl which is mono- to trisubstituted by $C_1$- to $C_4$-alkyl.

Alkenyl carboxylates III which may preferably be mentioned are: vinyl formate, vinyl acetate, vinyl propionate, vinyl stearate (vinyl octadecanoate), vinyl pivalate (vinyl 2,2-dimethylpropionate) and vinyl 4-tert-butylbenzoate.

The alkenyl carboxylates III are commercially available or can be prepared by known methods, for example by addition of carboxylic acids to acetylene or by acetoxylation of ethylene (Industrielle Organische Chemie (Industrial Organic Chemistry), 2nd edition, 1978, Verlag Chemie, pages 217 to 223).

Azoles II which may preferably be mentioned are: imidazole and 1,2,4-triazole.

These compounds are also commercially available or obtainable by known methods.

The products of the formula I are sought-after intermediates. N-Alkenylazoles, in particular the N-alkenylimidazoles, can be polymerized in a known manner. These polymers, in particular from N-vinylimidazole and N-vinyl-2-methylimidazole, are used, for example, as washing aids.

EXAMPLES

Examples 1 to 4

The azole II, the alkenylcarboxylate III and the base were reacted in the amounts indicated in Table 1a at the temperatures mentioned there and 1 bar. The amount of the quaternary salt indicated in Table 1b was then added without isolation and the temperature raised as is evident from Table 1b. The course of the reaction was monitored by gas chromatography. After reaction was complete, isolation was carried out by distillation.

The details can be seen from Table 1a and Table 1b:

TABLE 1a

| Example No.: | Azole II [mmol] | Ester III [mmol] | Base [mmol] | Temperature [°C.] |
|---|---|---|---|---|
| 1 | 300 mmol Imidazole | 360 mmol Vinyl formate | 300 mmol Triethylamine | 50 |
| 2 | 300 mmol Imidazole | 300 mmol Vinyl acetate | 150 mmol Triethylamine | 60 |
| 3 | 300 mmol 2-Methyl-imidazole | 300 mmol Vinyl acetate | 150 mmol Triethylamine | 60 |
| 4 | 300 mmol Benzimidazole | 500 mmol Vinyl formate | 500 mmol Dimethyl-cyclohexyl-amine | 60 |
| 5 | 300 mmol 4-Methyl-imidazole | 300 mmol Vinyl propionate | 300 mmol Triethylamine | 90 |
| 6[a] | 1 mol 1,2,4-Triazole | 1.1 mol Vinyl acetate | 0.5 mol 4-N,N-Di-methylamino-pyridine | 80 |

[a] addition of 100 g THF

TABLE 1b

| Example No.: | N,N-Dimethylpiper-idinium chloride (quaternary salt) | Temperature [°C.] | Alkenylazole I | Yield [%] |
|---|---|---|---|---|
| 1 | 0.33 | 140 | N-Vinylimidazole | 85 |
| 2 | 0.33 | 130 | N-Vinylimidazole | 92 |
| 3 | 0.5 | 140 | N-Vinyl-2-methylimidazole | 89 |
| 4 | 0.5 | 150 | N-Vinylbenzimidazole | 87 |
| 5 | 0.33 | 140 | N-Vinyl-2-methylimidazole | 91 |
| 6 | 1.5 | 150[b] | N-Vinyltriazole | 87 |

[b] after distilling off the solvent THF

We claim:

1. A process for preparing N-alkenylazoles of the general formula I

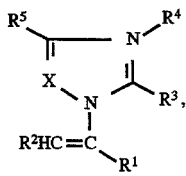

where

X is CH—$R^6$ or nitrogen, $R^1$ and $R^2$ are hydrogen or $C_1$- to $C_8$-alkyl, $R^3$, $R^4$, $R^5$ and $R^6$ are hydrogen, $C_1$- to $C_{40}$-alkyl, $C_2$- to $C_{40}$-alkenyl, $C_3$- to $C_{20}$-cycloalkyl, $C_4$- to $C_{20}$-alkylcycloalkyl, $C_4$- to $C_{20}$-cycloalkylalkyl, aryl, $C_7$- to $C_{20}$-alkylaryl or $C_7$- to $C_{20}$-aralkyl, or aryl, $C_7$- to $C_{20}$-alkylaryl or $C_7$- to $C_{20}$-aralkyl which are mono- to pentasubstituted by $C_1$- to $C_8$-alkyl, $C_1$- to $C_8$-alkoxy or halogen, or $R^3$ and $R^4$ or $R^4$ and $R^5$ or $R^5$ and $R^6$ together are a $C_2$- to $C_{10}$-alkylene chain which is unsubstituted or mono- to hexasubstituted by $C_1$- to $C_8$-alkyl by reaction of azoles of the general formula II

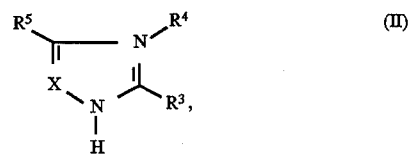

where X, $R^3$, $R^4$ and $R^5$ have the abovementioned meanings, with an alkenyl carboxylate of the general formula III

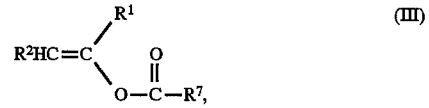

where $R^1$ and $R^2$ have the abovementioned meanings and $R^7$ is hydrogen, $C_1$- to $C_{40}$-alkyl, $C_3$- to $C_{20}$-cycloalkyl, $C_4$- to $C_{20}$-alkylcycloalkyl, aryl, $C_7$- to $C_{20}$-alkylaryl, $C_7$- to $C_{20}$-aralkyl, or aryl or $C_7$- to $C_{20}$-aralkyl which is mono- to trisubstituted by $C_1$- to $C_8$-alkyl, at from 0° to 180° C. and from 0.01 to 10 bar, which comprises carrying out the reaction in the presence of a base and of a quaternary salt.

2. A process for preparing N-alkenylazoles as claimed in claim 1, wherein $R^3$, $R^4$, $R^5$ and $R^6$ are hydrogen or $C_1$- to $C_{20}$-alkyl.

3. A process for preparing N-alkenylazoles as claimed in claim 1, wherein $R^3$, $R^4$, $R^5$ and $R^6$ are hydrogen or $C_1$- to $C_{12}$-alkyl.

4. A process for preparing N-alkenylazoles as claimed in claim 1, wherein $R^3$, $R^4$, $R^5$ and $R^6$ are hydrogen.

5. A process for preparing N-alkenylazoles as claimed in claim 1, wherein $R^1$ and $R^2$ are hydrogen.

6. A process for preparing N-alkenylazoles as claimed in claim 1, wherein $R^7$ is hydrogen, $C_1$- to $C_{20}$-alkyl, $C_3$- to $C_8$-cycloalkyl, aryl, $C_7$- to $C_{20}$-alkylaryl or $C_7$- to $C_{20}$-aralkyl.

7. A process for preparing N-alkenylazoles as claimed in claim 1, wherein the reaction is carried out at from 40° to 150° C.

8. A process for preparing N-alkenylazoles as claimed in claim 1, wherein the reaction is carried out at from 50° to 120° C.

9. A process for preparing N-alkenylazoles as claimed in claim 1, wherein the reaction is carried out at from 0.1 to 2 bar.

10. A process for preparing N-alkenylazoles as claimed in claim 1, wherein the reaction is carried out at atmospheric pressure.

11. A process for preparing N-alkenylazoles as claimed in claim 1, wherein the molar ratio of the alkenyl carboxylate III to the azole II is from 0.1:1 to 10:1, the molar ratio of said base to the azole II is from 0.1:1 to 10:1 and the molar ratio of said quaternary salt to the azole is from 0.0001:1 to 5:1.

12. A process for preparing N-alkenylazoles as claimed in claim 1, wherein the molar ratio of the alkenyl carboxylate III to the azole II is from 0.9:1 to 5:1, the molar ratio of said base to the azole II is from 0.2:1 to 4:1 and the molar ratio of said quaternary salt to the azole is from 0.1:1 to 0.8:1.

13. A process for preparing N-alkenylazoles as claimed in claim 1, wherein the molar ratio of the alkenyl carboxylate III to the azole II is from 1:2 to 1.2:1, the molar ratio of said base to the azole II is from 0.2:1 to 2:1 and the molar ratio of said quaternary salt to the azole is from 0.001:1 to 0.4:1.

14. A process for preparing N-alkenylazoles as claimed in claim 1, wherein the reaction is carried out in the presence of an inert solvent added to the reaction mixture in an amount of from 5 to 300% by weight.

15. A process for preparing N-alkenylazoles as claimed in claim 1, wherein the amount of inert solvent added is from 10 to 100% by weight.

16. A process for preparing N-alkenylazoles as claimed in claim 1, wherein the amount of inert solvent added is from 10 to 30% by weight.

* * * * *